(12) United States Patent
Schwarz

(10) Patent No.: US 6,842,250 B2
(45) Date of Patent: Jan. 11, 2005

(54) DEVICE FOR A QUANTIFIED DETERMINATION OF THE QUALITY OF SURFACES

(75) Inventor: Peter Schwarz, Geretsried (DE)

(73) Assignee: BYK-Gardner GmbH (DE)

( * ) Notice: Subject to any disclaimer, the term of this patent is extended or adjusted under 35 U.S.C. 154(b) by 341 days.

(21) Appl. No.: 09/736,110

(22) Filed: Dec. 13, 2000

(65) Prior Publication Data
US 2002/0071124 A1 Jun. 13, 2002

(51) Int. Cl.[7] .................. G01N 21/00; G01N 21/55; G01N 21/25
(52) U.S. Cl. .................. 356/445; 416/73
(58) Field of Search .................. 356/73, 416, 417, 356/445, 600

(56) References Cited

U.S. PATENT DOCUMENTS

| | | | | |
|---|---|---|---|---|
| 4,699,510 A | * | 10/1987 | Alguard | 356/417 |
| 4,886,355 A | * | 12/1989 | Keane | 356/73 |
| 5,377,000 A | * | 12/1994 | Berends | 356/73 |
| 5,701,173 A | * | 12/1997 | Rioux | 356/73 |
| 5,991,021 A | * | 11/1999 | Mukherjee et al. | 356/73 |
| 6,024,020 A | * | 2/2000 | Romano et al. | 356/417 |
| 6,122,042 A | * | 9/2000 | Wunderman et al. | 356/73 |
| 6,344,641 B1 | * | 2/2002 | Blalock et al. | 250/205 |
| 6,444,476 B1 | * | 9/2002 | Morgan | 250/459.1 |

* cited by examiner

Primary Examiner—Georgia Epps
Assistant Examiner—Alicia M. Harrington
(74) Attorney, Agent, or Firm—Raymond Sun

(57) ABSTRACT

The present invention relates to a device and a method for determining the quality of surface. An illuminating light source radiates light at a predetermined angle onto the measurement surface. An optical detecting device receives the light reflected from said measurement surface and converts same into an electrical measurement signal. A processor controls the measurement sequence and evaluates the measurement results, which are emitted via an output device. The illuminating light source comprises at least one light-emitting diode. The light emitted comprises at least blue, green and red spectral components in the visible range of the spectrum. A filter is provided in the path of radiation between the light source and the photosensor.

35 Claims, 5 Drawing Sheets

DEVICE FOR A QUANTIFIED DETERMINATION OF THE QUALITY OF SURFACES

BACKGROUND OF THE INVENTION

The present invention relates to a device and a method for determining the quality of surfaces, respectively the visual properties of surfaces.

The present invention relates in particular to a device and a method for the determining of the color and the color properties of surfaces.

The quality, respectively the visual properties of a surface, is to be generally understood here as being those physical properties of a surface which determine the appearance of a surface for a human observer.

Besides for color, respectively impression of color, these properties also include gloss, haze, distinctness of image (DOI), color brightness as well as surface texture and orange peel, etc.

The color of a surface is an especially important criterion for the assessing of surface quality, because the color, respectively impression of color, is a decisive feature for the overall impression of a product in the case of numerous consumer and technical products.

In many fields during the manufacturing of a product, it is crucial to ensure that the color of the product being manufactured does not change during the course of production. Such changes in product color can result from environmental conditions changing during the course of production (temperature, moisture, surface nature, etc.). In order to avoid such changes in color, manufacturing equipment must be monitored continuously or at regular intervals and products must be measured individually with respect to the nature of their surface.

For this reason, surface measuring and color measuring devices have become known in the prior art which can determine the visual properties of product surfaces. Many known measuring devices are however of large-scale size and represent great expenditure and expense in their acquiring and operating. Other known measuring devices are portable, yet provide only insufficient precision or accuracy.

It is therefore the task of the present invention to provide a device and a method of the type as indicated above to enable a reproducible and quantified evaluation of the quality of surfaces.

A further aspect of said task is to provide a device which is small and simple in its construction so that a user can effortlessly take it with him and can use it for determining the quality of a surface without the need to utilize any other auxiliary contrivances.

This task is solved in accordance with the present inventive device as defined in claim 1.

The inventive method comprises the subject matter of claim 35. Preferred embodiments of the invention constitute the subject matter of the subclaims.

SUMMARY OF THE INVENTION

A device according to the present invention for the quantified determination of the quality of a surface comprises a first optical means having an illuminating means, its emitted light directed at a predetermined angle to the measurement surface. A second optical means, directed at a predetermined angle to the measurement surface, receives a portion of the light reflected from the measurement surface. At least one photosensor is arranged in said second optical means which emits an electrical measurement signal which is characteristic of the light received by said second optical means.

A control and evaluation means is provided for controlling the measurement sequence and evaluating the measurement results and comprises at least one processor means and at least one memory means. An output means serves to display the measurement results and/or the evaluated data.

The illuminating means comprises at least one light source, whereby at least one of said light sources is a light-emitting diode (LED). The light emitted by the illuminating means exhibits a spectral characteristic which comprises at least the blue, green and red spectral components of the visible spectrum.

A filter means is further provided which is arranged in the path of radiation between the light source and the photosensor, whereby said filter means may be arranged either in the first or in the second optical means or at any other appropriate position in the path of radiation. It is also possible to provide several filter means, whereby a first filter means spectrally filters the light emitted from the at least one light source of the illuminating means of said first optical means and a second filter means is arranged in the path of radiation in front of the photosensor and likewise spectrally filters the light reflected by the measurement surface.

The evaluation means evaluates the reflected light and derives therefrom at least one parameter which characterizes the surface.

The device according to the present invention has numerous advantages.

A device in which a first optical means is provided with an illuminating means having light consisting of blue, green and red spectral components in the visible spectrum is highly advantageous since this then also allows for determining, for example, the color of a surface.

That the illuminating means in the inventive device has at least one light source rendered as an LED is of great advantage since at least one light source is then configured to be substantially resistant to aging.

In a preferred embodiment of the present invention, at least one of said at least one characteristic parameter is the color of the measurement surface. The inventive device is particularly well-suited for the determining of a color parameter of a surface. The inventive device can be of compact configuration and is then, e.g., readily portable. This enables also carrying out a determination of surface color at poorly accessible spots.

In another preferred embodiment of the present invention, the characteristic parameter to be determined from the surface to be measured is one taken from among a group of parameters which includes gloss, haze, distinctness of image, orange peel and fluorescence parameters and characteristic values, etc.

The inventive device is preferably suited for the determining of two or more different characteristic parameters of the surface to be examined.

In a preferred embodiment of the invention, a parameter encompasses a plurality of characteristic values which each characterize a reflectivity or remission capability of the measurement surface. It is then fundamentally preferred here that each characteristic value is preferably characteristic of a spectral reflective or remission capability at one wavelength band each. Preferably, the plurality of characteristic values of said parameter describes the spectral progression of the reflectivity or remission capability of the surface at a predetermined wavelength band.

Such a configuration is highly advantageous since the parameters to be determined comprise a plurality of characteristic values which characterize the spectral dependency of the surface properties to be determined to the wavelength.

Essentially, each of the characteristic values is then characteristic for a certain wavelength interval, whereby individual wavelength bands may also overlap.

BRIEF DESCRIPTION OF THE DRAWINGS

Further advantages, features and application possibilities of the present invention will now be specified in the following description of embodiments in conjunction with the drawings, which show.

DETAILED DESCRIPTION OF THE INVENTION

Figure 1:
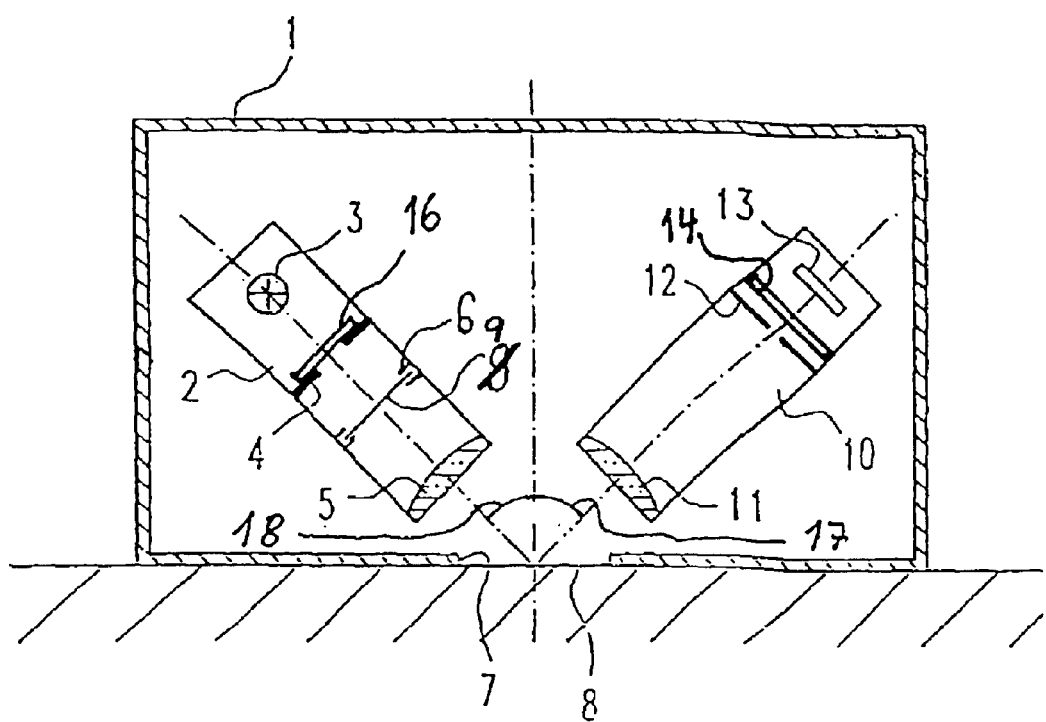
FIG. 1 a cut-away view of a device according to a first embodiment of the present invention.

A first embodiment will now be described with reference to FIG. 1.

Measuring device 1 is provided with a housing which is placed upon the surface to examined, respectively measurement surface 8. A first optical means 2 comprises an illuminating means 3 of one or more light source(s) 3, the light thereof directed to said measurement surface at an angle 18 from the perpendicular to the measurement surface. Said first optical means furthermore comprises a scattering means having a diffusor retainer 4 and a diffusor 16, whereby said diffusor retainer 4 simultaneously serves as an aperture for the radiation emitted from light source(s) 3.

A filter means is arranged in the further downstream path of radiation from light source(s) 3 to the surface to be measured 8 which comprises a filter retainer 6 and a filter element 9, which influences the light emitted from light source 3 according to predetermined filter properties. A lens 5 in the first optical means parallelizes the emitted light before it impinges the surface to be examined 8.

A second optical means 10 provided in the device is directed to the measurement surface at an angle 17 to the perpendicular, whereby said angles 17 and 18 in the present embodiment are both 45°, an angle especially well-suited for measurements of gloss. For other desired measurement variables such as, for example, color, one simply selects the appropriate different angle as fundamentally known in the state of the art. The light reflected from surface 8 is at least partially received by the second optical means 10 and focused onto a slot in an aperture 12 by a lens 11 of the second optical means, said slot serving as the inlet slot for a transmittance grid 14 which selectively splits the incident radiation spectrally and directs same to the line sensor 13 arranged in second optical means 10.

The spectral splitting element 14 represented in FIG. 1 is rendered as a volume transmittance grid. It is however just as feasible to use a reflection grid having readily variable beam guiding.

In the present embodiment, grid 14 makes use of diffraction to split incident light into spectral components, whereby different wavelengths of the incident light are deflected in highly differing fashion to sensor 13 so that photosensor 13, configured as a diode array or as a CCD sensor, receives different wavelengths at different areas. The individual elements of sensor 13 receive radiation of different wavelengths in the presently relevant visible part of the spectrum between 400 and 700 Nm.

The measurement signals of the individual photosensitive elements of said sensor 13 are electrically ascertainable individually, respectively can be separately evaluated, so that the relative spectral remission capability, respectively reflectivity of the surface, is available as a measurement result subsequent the measuring. To this end, the device is calibrated at least once with one or several reference surfaces, whereby one of said calibration surfaces with respect to, for example, measurement of gloss, may be preferably an ideally reflective surface.

Figure 3:
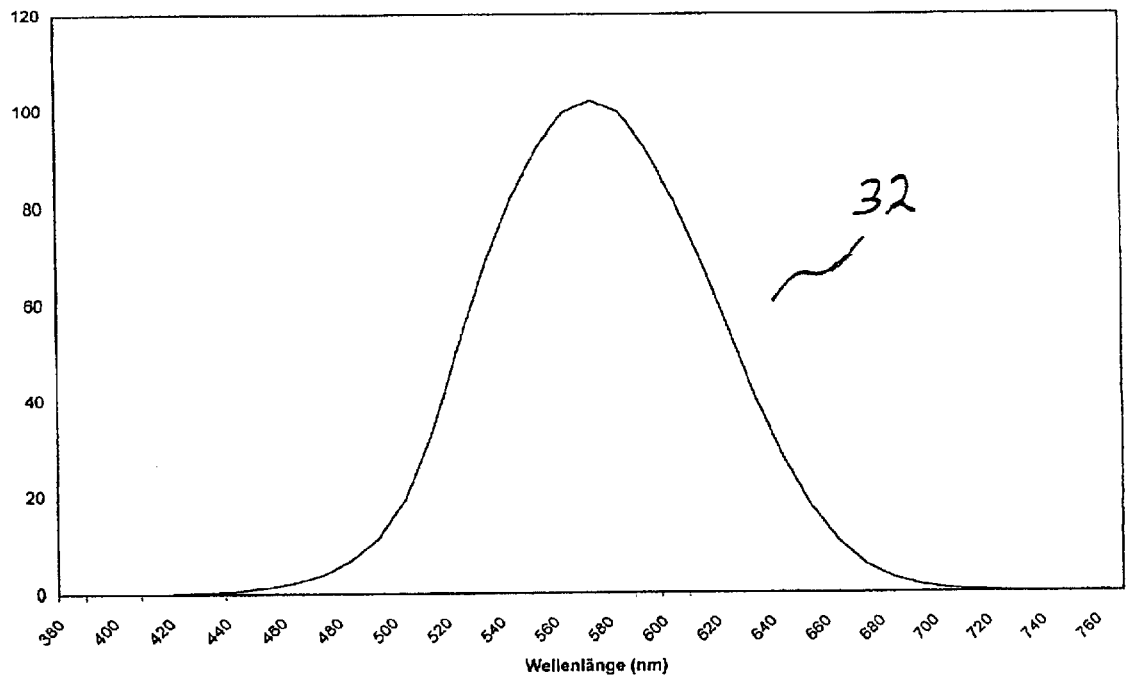
FIG. 3 a predetermined spectral distribution of intensity.

Illuminating means 3 in the present embodiment comprises a halogen light source and a plurality of light-emitting diodes (LEDs) in order that the spectrum of the light radiated by said illuminating means 3 approaches the spectral distribution as represented in FIG. 3. While the halogen light source emits radiation in essentially the entire spectral range, the individual LEDs serve to amplify individual spectral regions selectively.

Figure 4A:
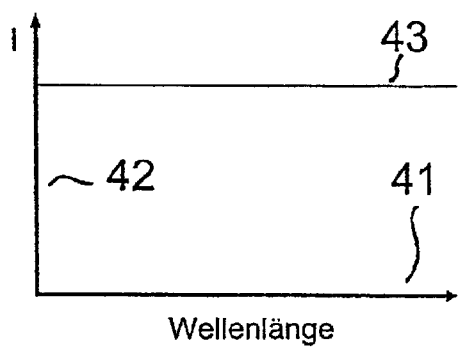
FIG. 4A another predetermined spectral distribution of intensity across a wavelength.
Figure 4B:
FIG. 4B a spectral distribution of the sensor signals across a wavelength.

In accordance with another configuration of the present embodiment, the individual light sources of illuminating means 3 are such controlled that a distribution of intensity as depicted in FIG. 4A is essentially attained at said sensor. Spectral distribution 43 depicted in FIG. 4A is plotted as intensity 42 across wavelength 41 and on a constant level across the relevant wavelength band independent of wavelength so that the spectral intensity of the light emitted at different wavelengths by illuminating means 3 is independent of wavelength.

In a further configuration of the present embodiment, the light sources of illuminating means 3 are such controlled that the electric signal of the individual photosensors, respectively the electrical measurement signal of the sensors converted into digital signal path 44, exhibits an essentially constant numerical magnitude across wavelength 41. This configuration allows the realizing of the signal of the individual sensors as independent of wavelength with an ideally reflecting surface and consequently an essentially constant and maximally high signal-to-noise ratio is achieved over an essentially constant noise level across the wavelength.

Filter means 9 is configured as an optical filter which absorbs the specific wavelength bands corresponding to the desired spectral distribution in order to achieve a spectral distribution of intensity in accordance with FIG. 3 or FIG. 4A.

While the second optical means in the present embodiment is directed at an angle of 45° to the measurement surface, it is also possible to align the second optical means perpendicular to the surface to be measured in order to measure part of the diffuse reflected light and not the directional reflected light.

Figure 2A:
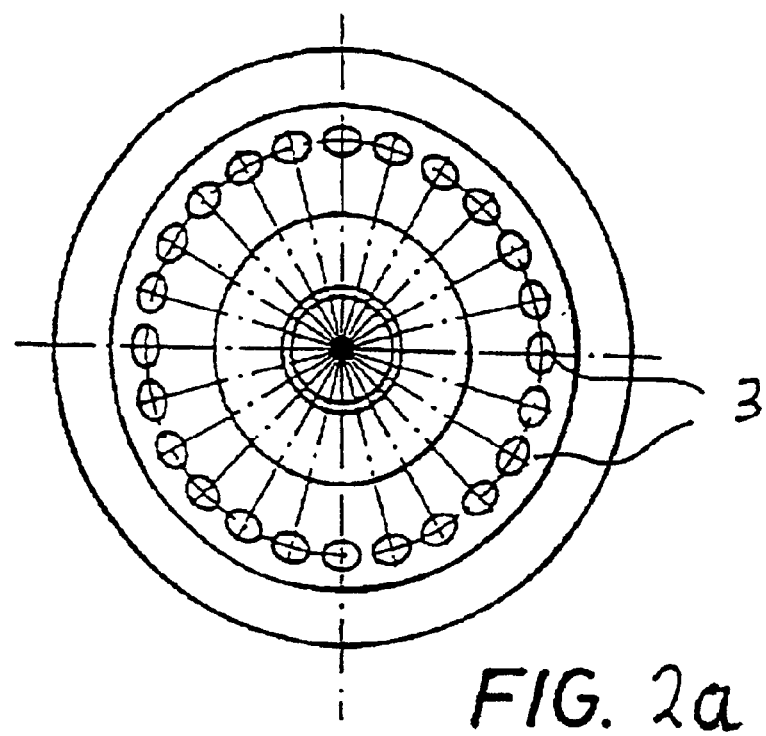
FIG. 2A an underside view of a further embodiment of the inventive device.
Figure 2B:
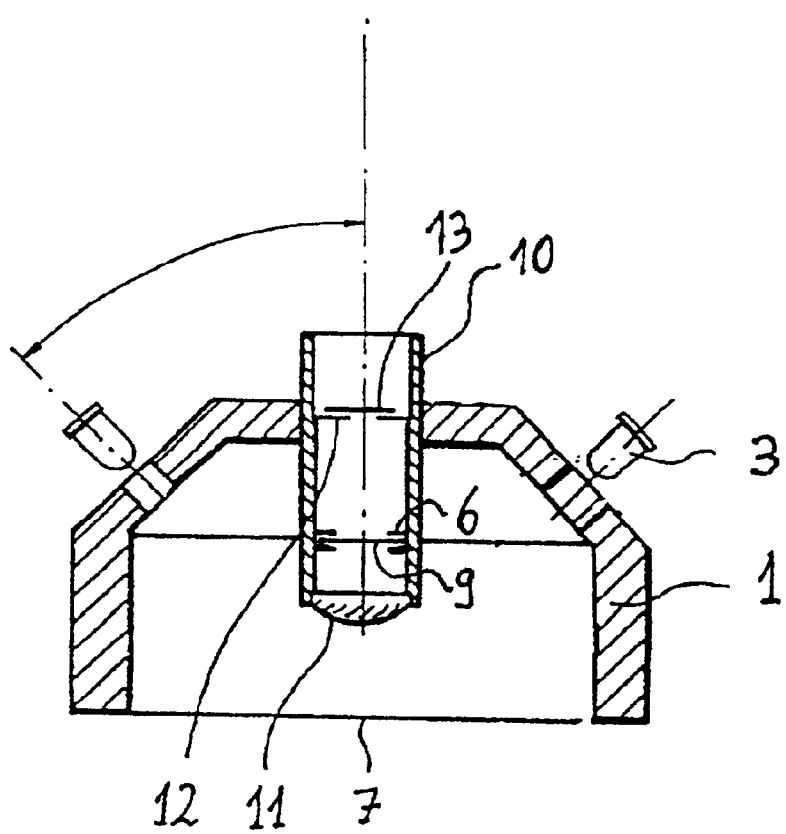
FIG. 2B a cross-sectional view of the device in accordance with FIG. 2A.

FIGS. 2A and 2B illustrate a further embodiment of a color measuring device in accordance with the present invention.

The measuring device is depicted in an underside view in FIG. 2A and is of annular shape in this view. A plurality of LEDs 3 of illuminating means 3 are arranged evenly at a constant radius around the circumference and, as is evident from FIG. 2B, are directed at an angle of 45° to the surface to be measured and illuminate the focal point below the device.

In the present embodiment, the second optical means is arranged perpendicular to the surface to be measured 7 and receives a portion of the diffuse reflected light of light sources 3. The light received by said second optical means 10 is focused by inlet lens 11 and passes through an opening in aperture 12.

An optical grid, a color filter or a color filter wedge can be provided behind aperture 12 in the further progressing path of radiation in order to split the incident radiation spectrally before it impinges sensor 13.

In contrast to the first embodiment, the illumination means 3 in the present second embodiment is arranged in circular fashion above the measurement surface to be examined so that the light emitted from the individual light sources 3 of illuminating means 3 is directed in a conical fashion toward the measurement surface to be examined, wherein the top of the cone defines the point of surface measurement.

All the light sources in the present embodiment are rendered as LEDs, whereby said LEDs emit spectrally different radiation and 24 LEDs in total are employed. Hence, there are three of each type of LED 3 in the present embodiment. Eight different LEDs respectively are arranged adjacent one another across the circumferential angle and the 24 LEDs are such arranged that the same type of light source is disposed at every 120° around the circumference. In another embodiment, 30 LEDs of 10 different diodes are employed.

It is however pointed out that a number of light sources which deviates from the above may also be employed, as long as each wavelength band exhibits considerable intensity in the visible part of the spectrum.

In the present embodiment, several circuitry, respectively control variations are provided for the individual light sources. In a first control variation, all LEDs are operated simultaneously during a measurement and their intensity is controlled in such a way that a relative spectral course of intensity is yielded which coincides essentially with the relative spectral course of intensity 32 depicted in FIG. 3. Spectral course of intensity 32 corresponds to a spectral course of intensity of the normal light standard C of the Commission Internationale de l'Éclairage (CIE) weighted to the spectral visual sensitivity of a normal observer's light-adapted eye V (index λ). For attainment of a such spectrum, the intensities of the individual LEDs are controlled accordingly. Furthermore, a filter 9 in a filter retainer 6 is disposed in the second optical means 10 for adapting the spectral distribution.

Figure 6:
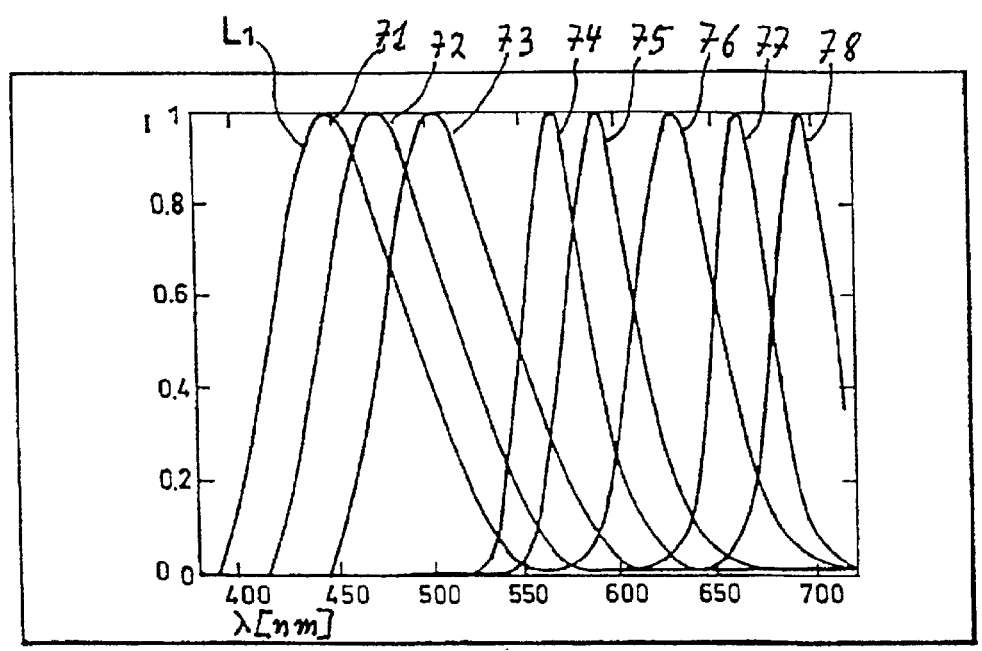
FIG. 6 the spectral distribution of intensity of different light-emitting diodes.

The spectral course of intensity of the individual diodes 71, 72, 73, 74, 75, 76, 77, 78 across the wavelength is plotted in FIG. 6. Each single LED (71–78) exhibits a relatively narrow spectral emission capacity, wherein the individual spectral ranges of the LEDs overlap so that radiation is emitted as a whole over the essential part of the visible spectrum.

According to a second circuitry, respectively measuring variation of the present invention, the individual LEDs are controlled relative the intensity of radiation so as to yield a spectral distribution of intensity as depicted in FIG. 4A, in which spectral distribution 43 is plotted across wavelength 41 and is constant across the wavelength in order to achieve a homogeneous illumination independent of wavelength.

In a further circuitry variation, the electric signals of the individual sensors, respectively the electrical signals of the individual sensors which have been converted into digital signals, are independent of wavelength when an ideally diffuse white reflective surface is to be measured. Subject to these prerequisites, a spectral digital sensor signal 44 is yielded which is substantially the same across the entire visible wavelength band. The integration time, exposure time respectively and/or amplification of the sensors is then controlled such that the individual sensors are operated taking advantage of their maximum dynamics.

In a technical circuiting measurement variation, the individual LEDs (additional) are operated successively in order to determine the effect of the individual radiating elements on the surface to be examined.

If, for example, fluorescent surfaces are illuminated with radiation of particular wavelengths, these surfaces change certain wavelengths into others and emit other preferred wavelengths.

Figure 5A:
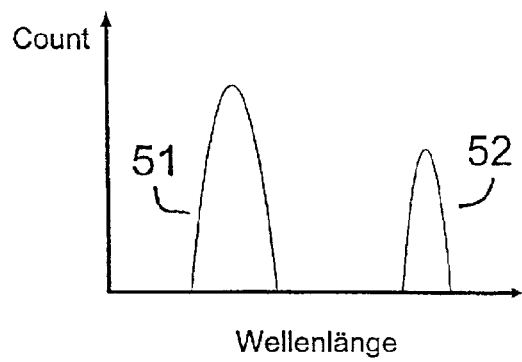
FIG. 5A the spectral distribution upon illuminating a fluorescent surface with a first light source.

The intensity distribution of a light source and the particular fluorescence-contingent spectral emission of a fluorescent surface is plotted schematically in FIG. 5A.

A source of radiation exhibits a spectral course of intensity 51 in a first wavelength band which, for example, may also correspond to one of the spectral courses of intensity 71–78 depicted in FIG. 6. The fluorescent surface emits a spectral intensity 52 when the surface is illuminated with appropriate wavelengths as, for example here, with spectral distribution 51.

Figure 5B:
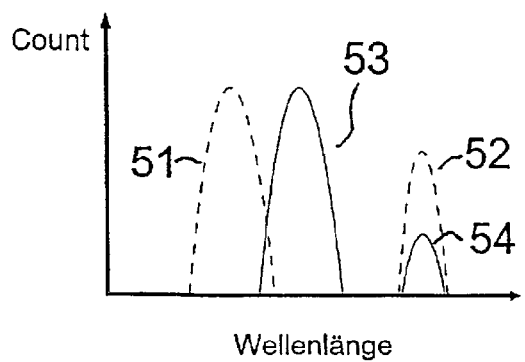
FIG. 5B the spectral signal distribution of a fluorescent surface upon illuminating with a different light source.

If the same surface is now illuminated with another source of light which exhibits a spectral intensity distribution 53 (cf. FIG. 5B) which differs from said first spectral distribution 51, the fluorescent surface can likewise emit a radiation 54. Provided spectral course of intensity 51 and 53 at least partially overlap and exhibit different intensities relative the wavelength which excites the surface to fluorescence, the spectral emission of surface 52 will deviate from spectral emission 54, as represented in FIG. 5B.

The excitation wavelength, respectively the excitation wavelength band for the exciting of the fluorescent surface can then be concluded from the spectral courses of intensity 52, respectively 54 emitted from the surface and especially the maximum height of the individual courses of intensity and from the spectral courses of emission of LEDs 51, 53 as employed, and can be defined both qualitatively as well as also quantitatively.

Figure 7:
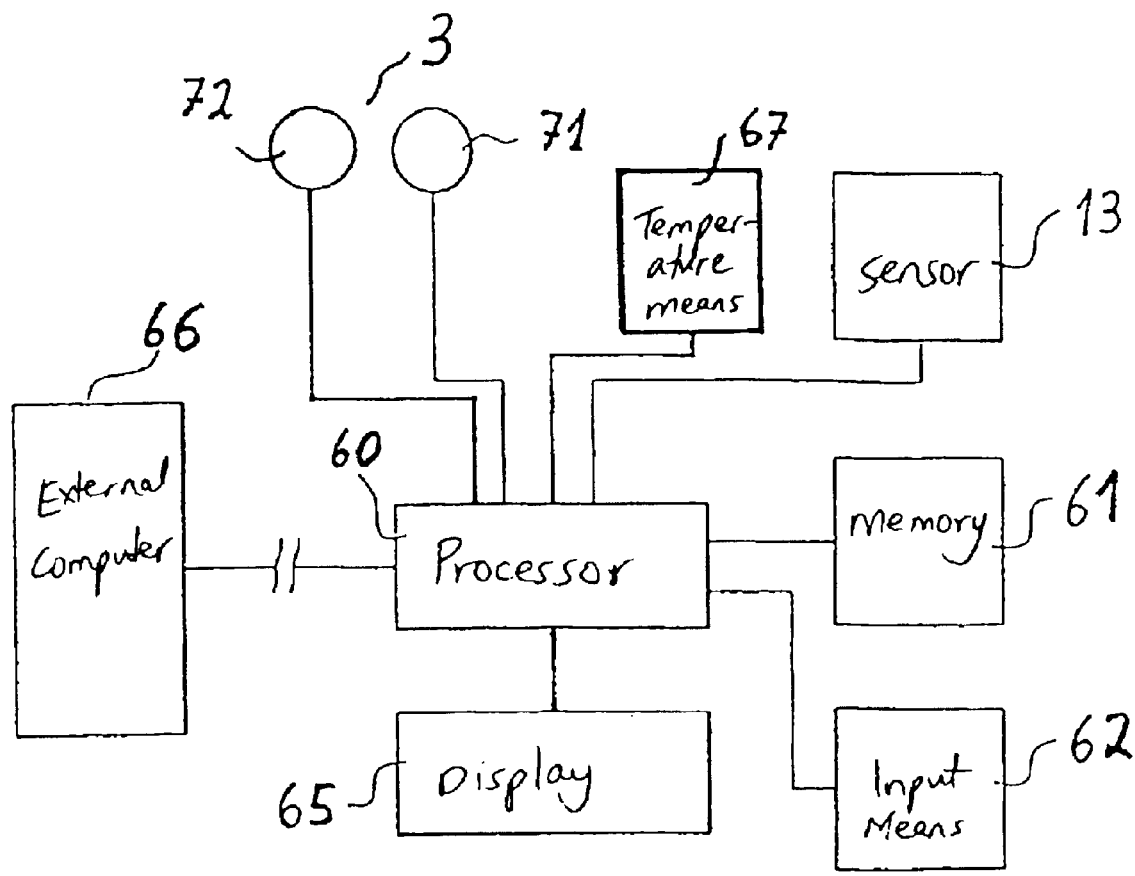
FIG. 7 the principal technical circuitry configuration of an embodiment.

FIG. 7 depicts the principal technical circuitry configuration of an inventive device in accordance with the described embodiments.

Control means 60 comprises a processor 60 which is linked with further elements in the control means.

By means of a program stored in memory means 61, control means 60 controls illuminating means 3 having light sources 3 and, as example 72, relative intensity, time of radiation and duration of radiation. The electric measurement signal received by photosensor 13 is digitized in processor 60 and, taking the measurement results of temperature means 67 monitoring the temperatures of the light sources and the photosensors into consideration, are then temperature-corrected and output to display 65 and/or filed in memory means 61.

Input means 62 serves for inputting control commands for the device as a whole. In this way, it is thus possible upon the actuating of certain switches (not shown) or by inputting of specific commands to, for example, modify the measurement method so that the intensity distribution of the emitted light is adapted to be in accordance with the light standard type C or the light standard type D65, or that the measurement characteristic is adapted to individual optics, light sources and sensors such that with ideally reflecting surfaces, the electric measurement signal for the various wavelengths of the photosensitive elements of photosensor 13 is essentially the same across the wavelength band.

Furthermore, the control means comprises a further means with which the device can be coupled to an external computer 66, whereby said coupling device is an electrical connection such as, for example, a serial interface or other standardized electrical connections. It is just as feasible that this interface is rendered as an infrared interface so that the connection to an external computer 66 can also be made across some distance without the need for cables.

As the foregoing configurations demonstrate, the present invention allows for the providing of a device for the measuring and evaluating of spectral radiations which enables the measuring of the spectral distribution of radiation to be realized at a relatively low expenditure and with the employing of a relatively small number of sources of radiation, respectively sensors. Based on its simple construction, the device can be configured to be relatively small and handy so that its utilization is not only possible within a laboratory setting, but which can also be employed directly during production processes in order to continuously monitor surface quality.

In accordance with a preferred embodiment of all the previously described embodiments and configurations of the invention, the illuminating means has two, three or a plurality of light sources which are rendered as conventional light sources as known in the prior art. Light sources employed in the illuminating means are preferably light-emitting diodes, thermal light sources such as normal bulb and halogen light sources or such as mercury, deuterium or xenon light sources and the like. The individual light sources may be coupled via one or several beam splitters.

According to an especially preferred embodiment of the present invention, at least two different light sources preferably differing in their spectral emissions are employed in the illuminating means.

This embodiment has the advantage that employing two spectrally different emitting light sources enables achieving high intensity across a greater wavelength band. A high intensity of radiation across a greater wavelength band increases the accuracy of the measurement since the signal-to-noise ratio is improved and hence also the accuracy in determining the parameter.

In accordance with one or several of the previously described embodiments, the light sources of the illuminating means have those spectral characteristics such that radiation may be emitted at essentially across the entire visible range of the spectrum. It is however also possible to determine a color parameter of a surface when the surface is illuminated by, for example, only three different appropriate wavelengths; however, measurement accuracy is increased when radiation is emitted at across the entire visible range of the spectrum.

In accordance with a particularly preferred embodiment of one or several of the previously described embodiments of the present invention, the illuminating means has a plurality of light sources, whereby preferably essentially all of said light sources are rendered as light-emitting diodes (LEDs).

Using LEDs as the light sources in the device is of great advantage since LEDs are small compact light sources requiring little space so that the device as a whole may be configured smaller than it can when using other light sources as known in the prior art. A further advantage of using LEDs, and particularly with their exclusive use, is that LEDs exhibit relatively negligible signs of aging and neither does the position of the light-emitting body, respectively light-emitting surface, fundamentally change due to aging or impact.

An age-contingent change in spectral emission occurs with conventional light sources disposed with an incandescent lamp or filament. Parts of the filament will evaporate and this evaporated material builds up on the inside of the filament's surrounding glass body, thus changing the spectral transmission of the glass body and hence the spectral emission of the light source. Another disadvantage of conventional light sources is that since the filament is basically spring-mounted above the connecting leads, its position can change over the course of time.

Just for this reason alone, a measuring device equipped with conventional lamps needs to be recalibrated from time to time in order to achieve a high precision and accuracy.

A further advantage of semi-conductor sources of radiation such as LEDs and the like is that these types of radiation sources emit a temporally stable signal shortly after switching them on while conventional bulbs need a considerably longer period of time in order to emit a temporally constant radiation due to thermal sources of radiation being subject to influences of temperature and thus the individual components such as the filament, the surrounding glass body, etc., first needing to warm up to working temperature before a temporally constant radiation can be emitted.

Another advantage when employing LEDs as light sources is that the power necessary for their operation is less than it is with conventional bulbs so that the device as a whole consumes overall less energy. This is especially advantageous when such a measuring device is to be rendered for portable operation and run from a battery or storage cell since the inventive device can then be configured to be smaller (smaller storage cells), respectively the measuring period can be extended by employing a set of batteries or storage cells.

In another preferred embodiment of the present invention, the inventive device comprises at least one thermal light source which is then preferably rendered as a halogen light source. The use of a halogen light source in addition to one, preferably several LED light sources also has advantages. The deliberate employing of one or several LEDs and, for example, one halogen light source can boost the specific spectral components in the visible range of the spectrum such that the spectral distribution of the emitted light exhibits a high intensity across a greater spectral range. A preferably uniformly high intensity across a large wavelength band in the relevant part of the spectrum grants a clear improvement in the signal-to-noise ratio and thus in the measurement result.

With conventional measuring devices, the progression of spectral intensity is often bell-shaped and falls off along both sides of the spectrum from a maximum spectral intensity at a given wavelength so that only a small intensity is achieved at one or both fringes of the spectrum. However, measurement accuracy is defined by, among other factors, the minimum intensity, respectively poorest signal-to-noise ratio in the relevant part of the spectrum.

If the minimum intensity is now increased in the relevant part of the spectrum by the use of a plurality of LEDs or by the use of at least one LED and a halogen light source, the measurement accuracy attained is likewise increased.

Just employing one LED in addition to a thermal light source also reduces the maintenance expenditure for such a device since at least one of the sources of radiation is subject to none or only minimal temporal changes so that the effects of time are less across the entire spectrum.

In a further preferred embodiment of the invention, the control means in the inventive device is configured in such a manner that same controls the measurement sequence such that at least one fluorescence parameter is definable for the measurement surface.

The determining of a fluorescence parameter for the measurement surface is highly advantageous. Conventional measuring apparatuses and devices measure, for example, the color of a measurement surface. However, the color of a measurement surface, respectively the visual impression of a measurement surface, also depends upon the type of radiation, respectively the spectral distribution of the radiation with which the measurement surface is illuminated. Yet many materials or surfaces have fluorescent properties which conventional measuring devices cannot determine. Should such types of surfaces be illuminated with radiation of a certain wavelength, the fluorescent properties induce the radiation given off by the surface to be at another wavelength. The visual impression of the surface is thus dependent upon the spectral distribution of the illuminating light sources. In a further preferred embodiment of the present invention, the control means controls the first optical means such that the light sources of said first optical means emit radiation simultaneously at least at one point in time so that light from all the light sources thus impinges the surface to be examined at said point in time.

The simultaneous illumination of the surface to be examined by essentially all light sources has the advantage that the individual light sources can then deliberately boost specific spectral regions so that the emitted light corresponds essentially, at least at this point in time, to a predetermined spectral distribution.

In another preferred embodiment of the present invention, the control means is rendered in such a manner that the first optical means of the device is controlled such that at least two spectrally different light sources of said first optical means emit radiation essentially one after the other, whereby preferably essentially all the spectrally differing light sources of said first optical means each emit radiation successively.

In the sense of the present invention, "spectrally differing light sources" is to be understood as that the spectral distribution of the intensity of the emitted radiation differs in at least one wavelength band so that one could describe the light sources as being linearly independent from one another.

For example, two identical halogen bulbs also radiate spectrally different distributions of intensity if they are operated at different voltages, since the temperature of the filament, and consequently the spectral characteristic of the thermal emitter, changes according to voltage. In the sense of the present invention, two such operationally different halogen bulbs are also spectrally differing emitters, respectively light sources.

Preferably, however, "spectrally differing light sources" is to be understood as that different types of light sources are used. For example, red, green, blue and yellow LEDs may be employed which emit radiation at differing spectral regions. It is however also possible to employ a thermal emitter such as a halogen or conventional light bulb which has several LEDs of differing colors.

Controlling such spectrally differing light sources such that radiation is emitted successively is also advantageous since the light from the spectrally differing light sources as reflected from the surface can be separately received and evaluated.

In a further preferred embodiment of the present invention, the control means controls the first and the second optical means such that one measurement is performed in which the at least two, preferably all light sources emit radiation simultaneously and that another measurement is performed in which at least two, preferably all spectrally differing light sources each emit radiation essentially one after the other respectively. The sequence of these measurements (measuring with several light sources simultaneously; measuring with the individual light sources successively) is contingent upon the given circumstances (nature of the surface, etc.).

Such a configuration is very advantageous since one measurement can be carried out on the one hand with the entire spectrum while it is also possible to measure individual spectral regions as well.

If at least one measurement is performed in which spectrally different light sources emit radiation successively, the individual measurement results of said individual light sources or said spectrally differing light sources are filed in the memory means of the device. Then at least one fluorescence parameter is preferably derived from said measurement results so that besides for a parameter such as, for example, surface color, at least one measure of the surface fluorescence is additionally determined. This determining of a surface's fluorescence properties is very advantageous because due to different products being used under the most differing of lighting conditions, an observer's impression of color also depends upon the fluorescent properties of the surface. A measurement surface can be better characterized by the determining of at least one fluorescence parameter.

In a further preferred embodiment of one or several of the previously described embodiments, a plurality of photosensors is provided, said photosensors preferably arranged adjacent to one another. Especially preferred is the arrangement into rows and/or into rows and columns, whereby particularly preferred is the use of a diode array or a CCD chip. Employing a plurality of photosensors arranged in a row or on a surface allows for the determining of a number of signals or portions of signals essentially simultaneously.

Employing a CCD chip offers the advantage that this type of sensor is universally prevalent and is of high and foremost quality.

Particularly when a plurality of photosensors is provided, but not limited thereto, a spectral means can be arranged in the path of radiation between the illuminating means and the photosensor(s) which then splits the incident radiation subject to wavelength. When employing a plurality of photosensors, it is then preferred that the spectral means splits the incident light such that the different wavelength bands of the incident light are then deflected to different photosensors, respectively different areas of a CCD array. The intensity on the individual photosensitive elements, respectively photosensors, is then representative of the different wavelength bands and the electrical output signal of an individual photosensor is characteristic of the radiation received at said corresponding wavelength band.

It is however also possible that only one photosensor (or only a few photosensors) are employed. In this case, it is then preferred when making use of a spectral means that either the illuminating means is arranged displaceably or rotatably and/or that the photosensor is arranged displaceably or rotatably. In such a configuration, the position of the illuminating means, respectively photosensor, is controlled such that the photosensor receives different wavelength bands one after the other so that a spectral distribution may be determined.

The provision of a spectral means in the inventive device is highly advantageous because this enables determining a spectral distribution of intensity to the light reflected from the surface.

Preferably, the spectral means comprises at least one (or several) spectral splitting elements which may be a spectral splitting element commonly employed in the prior art, as for example bending and/or refracting optical elements, absorbing elements, phase and amplitude grids, surface and volume grids, transmission and reflection grids, holographic optical elements, interference filters, color filters and color filter wedges, edges or cut-off filters, prisms and the like.

The spectral splitting element, respectively the spectral means, is arranged in the path of radiation in the inventive device, whereby it is possible that said spectral splitting element is rendered as a reflecting or transmitting element. When rendered as a reflecting element, a surface reflection grid as used in conventional spectrometers is preferred. When rendered as a transmitting spectral splitting element, a holographic transmission grid for example can be used, whereby the hologram substrate can be dichromate gelatine (DCG), polyvinyl alcohol or other such similar material. Color filters and color filter wedges are also particularly preferred.

It is also possible to arrange a plurality of spectral splitting elements in the inventive device, also differing ones, wherein one or several can be configured as transmitting elements and one or several as reflecting elements.

In accordance with a further preferred embodiment of the present invention, the filter means is configured in such a manner that the spectral characteristic of the incident light may be changed according to predetermined filter properties so that the spectral characteristic of the light preferably coincides substantially with a predetermined spectral distribution. The filter means can be rendered as a reflecting or transmitting filter means and preferably has at least one filter element. It is also possible that at least one reflecting as well as also at least one transmitting filter element are provided in the filter means which may also be arranged spatially separate from one another. Reflective filter elements or filter means reflect incident light and are often configured in such a manner that specific wavelength bands are reflected better than others so that the light reflected from the filter means exhibits a spectral distribution, spectral characteristic respectively, which coincides substantially with a predetermined spectral distribution.

Transmitting filter elements or filter means are usually so configured such that specific wavelength bands are transmitted better than others, whereby it is possible that specific wavelength bands may be absorbed or that specific wavelength bands are at least partially reflected or that specific wavelength bands are scattered to a greater or lesser degree. This makes it possible for the spectral distribution of the transmitted light to approach a predetermined spectral distribution.

Employing a filter means which adapts the spectral characteristic of the incident light to a predetermined spectral distribution is of great advantage in order to provide for the measurement conditions which will enable highly qualitative measurement results.

In accordance with a further particularly preferred embodiment of the inventive device, the predetermined spectral distribution is a standard distribution as has become standardized in the prior art. For example, illumination or measuring can transpire with the C light type standard, the D65 light type standard, the A light type standard or other such similar standards. Conducting a measurement with one of the afore-mentioned light standards is highly advantageous because this allows conducting the measurement procedure with spectral light distributions which are standardized and as close to reality as possible.

In accordance with another preferred embodiment, the predetermined spectral distribution has essentially a linear progression of intensity (particularly preferred, a constant progression of intensity) across the wavelengths in a predetermined region of the spectrum. Said predetermined wavelength band preferably comprises essentially at least the visible range of the spectrum between about 400 and 700 nm. Such a predetermined spectral distribution also offers advantages since particularly when illuminating or measuring with an essentially constant progression of intensity, a good signal-to-noise ratio is achieved across the relevant wavelength band.

In accordance with a further preferred embodiment of one or several of the previously described embodiments, the device and its individual elements are configured such that a spectral measurement characteristic is essentially proportional to a product of the spectral distribution of a standard light type and the visual sensitivity of the human eye.

The spectral measurement characteristic is hereby to be understood as the product of the spectral characteristic of the light radiated onto the measurement surface and the spectral sensitivity of the second optical means, respectively the sensor.

When this spectral measurement characteristic is proportional or essentially proportional to the product of the spectral distribution of a standard light type and the visual sensitivity of the human eye (visual sensitivity of the light-adapted eye or visual sensitivity of the dark-adapted eye), the device essentially reproduces the "natural sight process" of an observer.

Preferably, the spectral measurement characteristic is the product of the spectral characteristic values of all optical components involved, apart from the measurement surface itself. Thus, for example, the light radiated onto the measurement surface from the individual light sources is spectrally influenced by the individual optical elements in the first optical means while the spectral characterstic of the light reflected from the measurement surface is then influenced by the individual optical elements in the second optical means. The spectral measurement characteristic cited above takes all or essentially all spectral influences of the components involved into account.

In accordance with a further preferred embodiment, the above-cited spectral measurement characteristic, being a product of the spectral characteristic of the light emitted onto the surface and the spectral sensitivity of the second optical means, is essentially independent of wavelength in a predetermined region of the spectrum which preferably comprises the greater part of the visible spectrum (>50%; better: >80%); particularly preferred is the comprising of at least the visible range of the spectrum.

In accordance with the present preferred embodiment, the spectral measurement characteristic exhibits an essentially linear progression across the wavelength in the predetermined spectral region; particularly preferred is the spectral measurement characteristic exhibiting an essentially constant value in said wavelength band so that in the case of an ideally reflecting surface, the output signal, respectively sensors, are essentially independent of wavelength.

In the present preferred embodiment, the spectral distribution of the emitted light is preferably influenced in such a manner so as to balance to the spectral characteristics of the other optical components and the sensor(s). In those spectral regions in which the sensor exhibits a lower sensitivity, the intensity of the radiated light can be increased accordingly so that the intensity, respectively electrical output signal of the sensor(s), is essentially independent of the received light's wavelength.

Such an essentially constant spectral measurement characteristic has advantages particularly when making use of a diode array or a CCD chip because all the elements in the diode array are then boosted by the same amplification factor. In order to attain a signal-to-noise ratio which is as high as possible when employing a diode array, the exposure, respectively integration time is selected to be so high that individual elements emit a maximum signal. For example, should a diode array be illuminated with a normal bulb, the radiation emitted from the bulb normally exhibits a maximum in the red region of the spectrum at which conventional silicon cells likewise exhibit a maximum sensitivity.

The spectral measurement characteristic of such an illumination source with such a sensor thus exhibits a highly pronounced maximum in the red region of the spectrum, decreasing in the greater and lesser wavelengths. Only a low utility signal is then generated particularly in the blue range of the spectrum which can be of up to about one or several magnitudes less than the maximum utility signal. As a consequence, the signal-to-noise ratio deteriorates from the maximum of the spectrum by a factor of 10, 100 or more in the corresponding spectral region.

If the exposure, respectively integration time is now increased, the individual elements of the diode array depart from the linear area of activity and upon a further increase in the supplied quantity of light, respectively an increase in the exposure time, individual sensors are overridden when the light to be measured is split onto the individual sensors or elements of the diode array. When individual sensors are overridden, it can happen that the charging of an element of the diode array can encroach on a directly adjacent or nearby element so that the measurement result not only of the overridden element but also of the neighboring element(s) is inaccurate and faulty.

Should a spectral measurement characteristic now be employed for the measurement which exhibits an essentially constant progression across a predetermined wavelength interval, essentially all elements of the diode array will be modulated equally, which has the consequence of a significant increase in the poorest signal-to-noise ratio and, thus, in the quality of the measurement.

If individual photo sensors are employed, their signals are amplified in each case individually so that a spectral measurement characteristic having, for example, a distinctive dependence upon wavelength may also be used. But since a smaller effect is seen in the case of diffused light, it can also be advantageous in the present application example to keep the spectral measurement characteristic relatively constant in the relevant wavelength band. Should the radiation be split, for example, subject to wavelength and a sensor is provided for a wavelength band at approximately 400 nm, a 50% portion of the diffused light at, for example, the 700, 800 or 900 Nm wavelength band will lead to an proportionally greater distortion of the measurement results due to the fact that, for example, silicon-based sensors are more sensitive at this wavelength band.

For reducing the influence of diffused light, it is preferred that a filter element of the filter means essentially filters out radiation above the relevant wavelength band. If such a filter element is positioned in the path of radiation between the light sources and the surface to be measured, this offers the advantage that radiation of a higher wavelength band at which the sensors employed are often particularly sensitive essentially does not even reach the measurement surface in the first place and consequently cannot produce any diffused light in the second optical means.

On the other hand, it is also advantageous to arrange such a filter element in the second optical means so that the photosensors are essentially shielded from diffused light at such wavelengths which for example enter the device from the environment. Furthermore, such a filter element in the second optical means in front of the photosensor offers the advantage that radiation at these wavelength bands emitted by the measurement surface itself will be kept away from the photosensor.

It is also possible to arrange one filter element in the path of radiation between the light sources and the measurement surface and another filter element in the path of radiation between the measurement surface and the sensor, whereby the particular positioning of the filter elements in the first or second optical means may ensue at appropriate positions.

In accordance with a further preferred embodiment of the present invention, the measurement results from the sensor, respectively the signals of the sensors, are evaluated mathematically, whereby this evaluation may transpire according to the teaching proffered in WO 96/09524, respectively DE 44 34 168 A1, which is hereby included in the disclosure of the present invention. Such an evaluation makes use of different calibration standards and a number of light sources which are linearly independent and a number of sensors which likewise exhibit linearly independent spectral characteristics which can also be obtained via filters connected in series. Should m light sources and n different sensors be employed, m·n calibration standards can be measured and a linear equation system instituted. This linear set of equations can be used to determine the individual coefficients of the individual elements with respect to different wavelength bands so that the spectral remission capability or reflectivity of the surface to be measured can be determined with the coefficients ascertained during a measurement of a surface to be measured.

Determining the wavelength-contingent remission capability or reflectivity with the teaching disclosed in the cited documents enables increasing the resolution in the subpixel range particularly when employing a CCD or diode array.

In accordance with a further preferred embodiment of the present invention, the filter means is configured such that the spectral properties of at least one filter element are controllable. This enables the position of at least one filter element to be variable so that upon, for example, extracting said filter element from the path of radiation, the light used in the measurement procedure is no longer influenced.

It is however also possible to use a filter element which is variable during operation as to its spectral characteristic. Viable filter elements here are, for example, those based on LCD (liquid crystal display) technology. For example, in the case of color displays, certain selective colors can be displayed and with such computer LCD displays as already prevalent nowadays which are suitable, for example, for loading to an overhead projector, it is possible to depict basically any color desired. Such that it is likewise possible to selectively influence the spectral characteristic of the light transmitted through such a display. With such a filter element, the control means can control the filter element during operation of the device in such a manner that predetermined spectral properties of the filter element and consequently the measurement characteristic, respectively the device, are obtained.

Such a filter means, respectively such a filter element, allows the realizing of greatly differing spectral characteristics or spectral distributions to the light radiated onto the measurement surface.

It is possible to use a standard daylight distribution for measuring in a first measurement process and to control all the sensors in a second measurement process such that an ideally reflecting surface would yield the same output signal with all sensors.

If the surface is illuminated with daylight or with a light distribution which corresponds to the spectral distribution of daylight, the impression of color and also the fluorescence properties of the surface as they appear in the field can be determined On the other hand, a spectral characteristic which is essentially independent of wavelength offers the advantage of a signal-to-noise ratio which is as high as possible.

In the sense of the present invention, the designations "essentially linear" as well as "essentially constant" and the like are to be understood as achieving he best possible approximation to the given defaults, whereby certain deviating tolerations are allowable. For example, it may be possible that no appropriate light source has been provided for a certain spectral range so that light sources will be used which also emit in said spectral range, just not at maximum intensity. Then, considerable deviations from the intended spectral distribution, respectively spectral characteristic can be allowable in the sense of the present invention, as long as this achieves a better adapting than would be the case as, for example, with only one light source. This deviation can therefore amount to 50% or more; a deviation of <50% is however preferential and particularly preferred is <20% or <5% from the ideal line.

In another preferred embodiment of one or several of the previously described embodiments, it is particularly preferred that the spectral distribution of the light radiated from said illuminating means is controllable by means of said control means, whereby especially preferred is the selective influencing of individual light sources of said illuminating means so that at least the intensity of the individual light sources may be influenced and preferably also, even if customary in a smaller setting, the radiated wavelength, respectively wavelength band of individual or all light sources.

Such a configuration is highly advantageous since the spectral distribution of the light radiated onto the measurement surface can be adapted to a predetermined spectral distribution in a selective manner. For example, if several different colored LEDs are used as light sources, the intensity of the individual LEDs can be so coordinated with one another that the spectral distribution of the total emitted light corresponds to one of the predetermined spectral distributions.

In another preferred embodiment of the present invention, a diffusor means and an aperture means are disposed in the first optical means, whereby the diffusor means is preferably configured so as to achieve a homogeneous illuminating of the measurement surface. This allows slight deviations at the measurement site to be of no significance for the measurement results.

In another preferred embodiment of the present invention, the evaluation means is controlled via a program stored in the memory means and the evaluation means receives the measurement signals of the photosensors and evaluates same, whereby the measurement signals, respectively the characteristic reference values are preferably stored permanently in said memory means.

According to one or several of the preferred embodiments of the invention, the second optical means is directed at a different angle to the measurement surface than is the first optical means so chat the light emitted from the first optical means and reflected from the measurement surface has a different angle to the measurement surface than the angle between the light received by the second optical means and the normal to the measurement surface.

The individual optical means can be directed at any desired angle to the surface, although it is preferable that the angles are at 0°, 20°, 30°, 45°, 60° or 85° to the normal of the surface to be measured. A geometry of 0°/45° is particularly preferred especially for measurements of color wherein one optical means is aligned perpendicularly over the surface to be measured and the other optical means is directed at an angle of 45° to the surface to be measured.

In a further preferred embodiment of the present invention, each photosensor is disposed with at least two, preferably three or more photosensitive elements whereby their electrical output signals can be acquired individually and which differ in their spectral characteristics such that the color of the reflected light is ascertainable. An example of such a photosensor, respectively an array of photosensors, is a color CCD sensor.

In all of the foregoing embodiments described above, it is possible that at least one temperature measuring means respectively is disposed in as immediate proximity as possible to one or more light source(s) and/or one, several or all photosensor(s), provided for the determining of the characteristic temperature of each respective light source, respective photosensor or respective photosensitive element in order to enable a temperature-corrected determination of said at least one optical parameter. The temperature measuring means may comprise several (or just one) temperature sensors which are arranged, for example, as close as possible to the individual elements in order to avert to as great an extent as possible a falsifying distortion of the measurement results due to thermal capacities and thermal resistances. It is however also possible, with at least some of these elements, that the element itself is used to determine its temperature directly, as described, for example, in WO 96/09667 or DE 44 34 266 A1.

The determining of temperature or of the temperature of individual or of all the elements is highly advantageous because temperature-contingent spectral influencing variables can be taken into consideration and their influence on the measurement results hence essentially disregarded.

What is claimed is:

1. Device for the quantified determination of the properties of surfaces having:
   a first optical means comprising at least one illuminating means its light directed at a predetermined angle to a measurement surface which is a part of the surface to be measured, as well as a second optical means which is directed at a predetermined angle to the measurement surface and which receives the light reflected from said measurement surface, whereby said second optical means comprises at least one photosensor which emits an electrical measurement signal which is characteristic of said reflected light;
   a control and evaluation means provided for controlling the measurement sequence and evaluating the measurement results and which comprises at least one processor and at least one memory mean;
   an output means;
   wherein said illuminating means comprises at least one light source which is a light-emitting diode (LED),
   said light sources of said illuminating means exhibit spectral characteristics such that radiation is emitted essentially uninterruptedly across essentially the entire visible spectrum;
   wherein at least one intensity of one light source is controllable;
   whereby a filter means is provided which is arranged in the path of radiation between said light source and said photosensor, and
   wherein said evaluation means evaluates said reflected light and derives therefrom at least one parameter which characterizes said surface, in particular the fluorescence.

2. Device according to claim 1, characterized in that at least one of said at least one parameter is the color of said measurement surface.

3. Device according to claim 1, characterized in that at least one of said at least one characteristic parameter is taken from among a group of parameters which includes gloss, haze, fluorescence, distinctness of image (DOI) a representative measure of the typical wavelength and the amplitude of same (orange peel) of the surface topology of said measurement surface at a predetermined wavelength interval.

4. Device according to claim 3, characterized in that two, three or more characteristic parameters of said measurement surface are determined.

5. Device according to claim 1, characterized in that at least one of said at least one parameter comprises two, three or more characteristic values.

6. Device according to claim 1, characterized in that at least one of said at least one parameter comprises a plurality of characteristic values which characterize the reflectivity of said measurement surface, whereby preferably essentially each of said characteristic values is characteristic of a spectral reflectivity at one wavelength band each.

7. Device according to claim 1, characterized in that said illuminating means comprises a plurality of light sources, wherein each of said light sources is a type of light source which is taken from among a group of light sources which includes light-emitting diodes, thermal light sources such as normal and halogen bulbs or such as mercury, deuterium or xenon light sources.

8. Device according to claim 7, characterized in that said light sources of said plurality of light sources of said illuminating means are rendered as light emitting diodes.

9. Device according to claim 7, characterized in that said first optical means is controlled such that said light sources emit radiation essentially simultaneously which corresponds essentially to a predetermined spectral distribution.

10. Device according to claim 1, characterized in that said illuminating means comprises at least two light sources which differ in their spectral emissions.

11. Device according to claim 10, characterized in that said first optical means is controlled such that each spectrally differing light source of said first optical means emits radiation successively.

12. Device according to claim 10, characterized in that said control means controls said first and said second optical means such that a first measurement is conducted in which at least two light sources emit radiation simultaneously and that a second measurement is conducted in which at least two spectrally differing light sources emit radiation essentially successively.

13. Device according to claim 10, characterized in that said control means controls said measurement sequence such that one measurement is performed in which spectrally differing light sources emit radiation successively and the measurement results are filed in said memory means, and that said at least one fluorescence parameter is derived from said measurement results.

14. Device according to claim 1, characterized in that said illuminating means comprises at least one thermal light source which is preferably rendered as a halogen light source.

15. Device according to claim 1, characterized in that said control means controls the measurement sequence such that at least one fluorescence parameter is determined for the measurement surface.

16. Device according to claim 1, characterized in that a plurality of photosensors is provided, arranged adjacent to one another.

17. Device according to claim 1, characterized in that a CCD chip is disposed as said photosensor, on which the photosensitive elements are arranged in a row or in rows and columns.

18. Device according to claim 1, characterized in that a spectral means is arranged in the path of radiation between said illuminating means and said photosensor which splits the incident radiation subject to wavelength.

19. Device according to claim 18, characterized in that said spectral means comprises at least one spectral splitting element which is taken from among a group of spectral splitting elements which includes absorbing, bending and refracting optical elements, phase and amplitude grids, surface and volume grids, transmission and reflection grids, holographic optical elements, color filters, color filter wedges, prisms and the like.

20. Device according to claim 17, characterized in that said spectral means spectrally splits the incident light such that different wavelength bands of said incident light are deflected to different areas of said CCD array such that different photosensitive elements receive different wavelength bands.

21. Device according to claim 18 characterized in that said spectral means spectrally splits the incident light such that different wavelength bands of said incident light are deflected to different areas of said CCD array such that different photosensitive elements receive different wavelength bands.

22. Device according to claim 1, characterized in that said filter means changes the spectral characteristic of the incident light in accordance with predetermined filter properties such that the spectral characteristic coincides substantially with a predetermined spectral distribution.

23. Device according to claim 22, characterized in that said predetermined spectral distribution is a standard distribution which comprises a type of light taken from among a group of light standards which includes the C light type standard, the D65 light type standard, the A light type standard and other such similar standards.

24. Device according to claim 22, characterized in that said predetermined spectral distribution exhibits an essentially linear progression of intensity across the wavelengths in the visual range of the spectrum.

25. Device according to claim 1, characterized in that a spectral measurement characteristic, which is a product of the spectral characteristic of the light radiated onto said measurement surface and the spectral sensitivity of the sensor and the filter employed, is essentially proportional to the product of a spectral distribution of a light type standard and the visual sensitivity of the human eye.

26. Device according to claim 1, characterized in that a spectral measurement characteristic, which is a product of the spectral characteristic of the light radiated onto said measurement surface and the spectral sensitivity of the second optical means, yields a predetermined spectral progression upon a specific sampling.

27. Device according to claim 1, characterized in that said filter means comprises at least one or several filter elements which have predetermined spectral properties so that the light emitted from said illuminating means can be selectively influenced spectrally.

28. Device according to claim 27, characterized in that said filter means is configured such that the spectral properties of at least one filter element are controllable.

29. Device according to claim 1, characterized in that said spectral distribution of the light emitted by said illuminating means is controllable.

30. Device according to claim 1, characterized in that a diffusor means and an aperture means are disposed in said first optical means, whereby said diffusor means is configured so as to achieve a homogeneous illuminating of the measurement surface.

31. Device according to claim 1, characterized in that said evaluation means evaluates said measurement signals by means of a program stored in said memory means and/or stores same in said memory means.

32. Device according to claim 1, characterized in that the light emitted by said first optical means is directed to the surface at such an angle such that the light reflected directly from the measurement surface in accordance with the Fresnel reflection is at another angle with respect to the measurement surface than the angle between said measurement surface and the light reflected from said measurement surface as received by said second optical means.

33. Device according to claim 1, characterized in that at least one photosensor comprises at least tow, preferably three or more photosensitive elements, the electrical output signals of which can be acquired individually and which differ in their spectral characteristic such that the color of the reflected light is ascertainable as an optical parameter of said measurement surface.

34. Device according to claim 1, characterized in that at least one temperature measuring means is arranged in as immediate proximity as possible to at least one light source and/or at least one photosensor, provided for the determining of the characteristic temperature of each respective light source and/or each respective photosensor so as to enable a temperature-corrected determination of said at least one parameter.

35. Method for determining the quantified quality of surfaces when employing a device in accordance with claim 1, in which the device is aligned relative a measurement surface; and a first optical means having at least one illuminating means radiates light at a predetermined angle to a measurement surface; and a portion of the light reflected from said measurement surface is received by one of a second optical means which is directed at a predetermined angle to said measurement surface, wherein a photosensor of said second optical means emits an electrical measurement signal which is characteristic of said reflected light; and a control and evaluation means controls the measurement sequence and evaluates the measurement results and derives therefrom at least one parameter which characterizes said surface; and an output means outputs said measurement results.

* * * * *